US00PP20326P2

(12) United States Plant Patent
Knosher

(10) Patent No.: US PP20,326 P2
(45) Date of Patent: Sep. 22, 2009

(54) ***GAURA* PLANT NAMED 'BALTINCITE'**

(50) Latin Name: *Gaura lindheimeri*
Varietal Denomination: Baltincite

(75) Inventor: Lynne Knosher, St. Charles, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 12/218,449

(22) Filed: Jul. 15, 2008

(51) Int. Cl.
*A01H 5/00* (2006.01)

(52) U.S. Cl. ..... Plt./432

(58) Field of Classification Search ..... Plt./432
See application file for complete search history.

(56) References Cited

PUBLICATIONS

Canada Plant Breeders' Rights Application No. 08–6194 filed Feb. 28, 2008. Published information from web site attached http://www.inspection.gc.ca.

*Primary Examiner*—Kent L Bell
(74) *Attorney, Agent, or Firm*—Audrey Charles

(57) ABSTRACT

A new and distinct cultivar of *Gaura* plant named 'Baltincite', characterized by its white-colored flowers, dark green-colored foliage, and moderately vigorous, upright to semi-upright growth habit in the garden.

1 Drawing Sheet

Latin name of genus and species of plant claimed: *Gaura lindheimeri.*
Variety denomination: 'Baltincite'.

BACKGROUND OF THE INVENTION

The present invention relates to a new and distinct cultivar of *Gaura* plant botanically known as *Gaura lindheimeri* and hereinafter referred to by the cultivar name 'Baltincite'.

The new cultivar originated in a controlled breeding program in Elburn, Ill. during February 2004. The objective of the breeding program was the development of *Gaura* cultivars that continuously flower with attractive flower coloration, dark green-colored foliage, and a well-branched, upright to semi-upright habit in the garden.

The new *Gaura* cultivar is the result of cross-pollination. The female (seed) parent of the new cultivar is the proprietary *Gaura lindheimeri* breeding selection designated 0044-A2, not patented, characterized by its dark pink-colored flowers, dark green-colored foliage, and moderately vigorous, semi-upright growth habit. The male (pollen) parent of the new cultivar is the proprietary *Gaura lindheimeri* breeding selection designated 0017-A1-B2-A2-2, not patented, characterized by its white-colored flowers, medium green-colored foliage, and moderately vigorous, semi-upright growth habit. The new cultivar was discovered and selected as a single flowering plant within the progeny of the above stated cross-pollination during June 2005 in a controlled environment at Elburn, Ill.

Asexual reproduction of the new cultivar by terminal stem cuttings since June 2005 at Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Baltincite' as a new and distinct cultivar of *Gaura* plant:

1. White-colored flowers;
2. Dark green-colored foliage; and
3. Moderately vigorous, upright to semi-upright growth habit in the garden.

Plants of the new cultivar differ from plants of the female parent primarily in flower color and plant height. The new cultivar is shorter than the female parent. Plants of the new cultivar differ from plants of the male parent primarily in foliage color and branching characteristic. The new cultivar has more branches than the male parent.

Of the many commercially available *Gaura* cultivars, the most similar in comparison to the new cultivar is 'Whirling Butterflies', not patented. However, in side by side comparisons, plants of the new cultivar differ from plants of 'Whirling Butterflies' in at least the following characteristics:

1. Plants of the new cultivar begin to flower approximately 7 days earlier than plants of 'Whirling Butterflies';
2. Plants of the new cultivar have more inflorescences per plant with fully open flowers than plants of 'Whirling Butterflies'; and
3. Plants of the new cultivar have a glabrous upper leaf surface texture compared to a pubescent upper leaf surface texture for plants of 'Whirling Butterflies'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Baltincite'. The plants were grown in 4.5 inch pots for 6 weeks in a greenhouse at West Chicago, Ill. Plants were given one pinch at transplant.

DETAILED BOTANICAL DESCRIPTION

Figure 1:
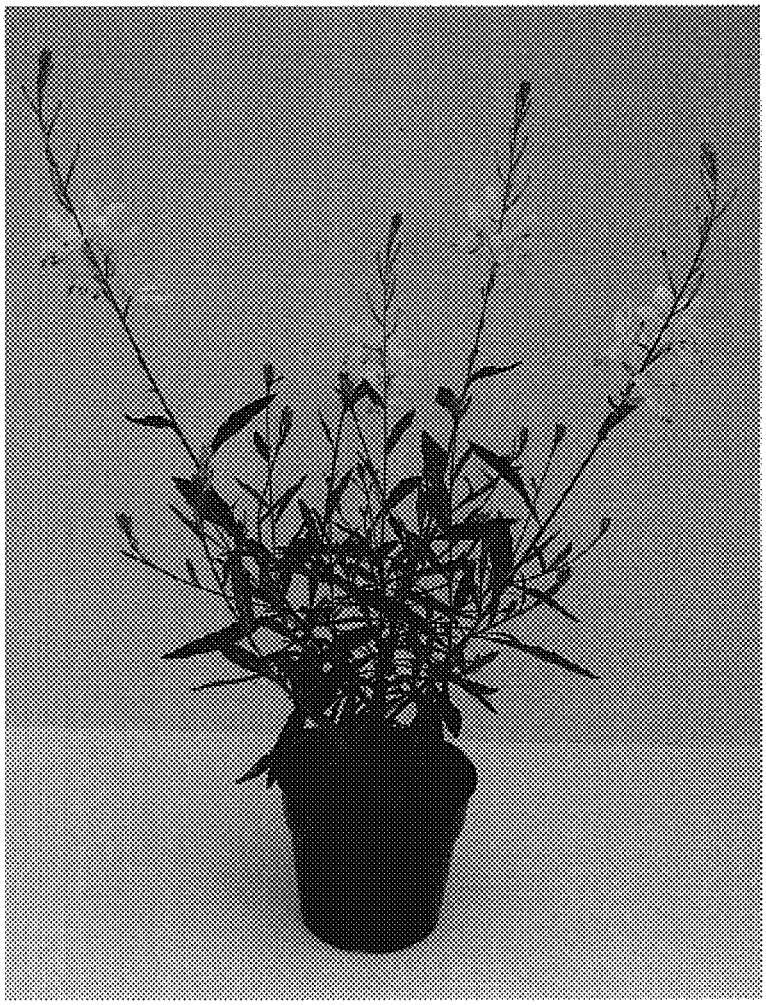
FIG. 1 illustrates a side view of the overall growth and flowering habit of 'Baltincite'.
Figure 2:
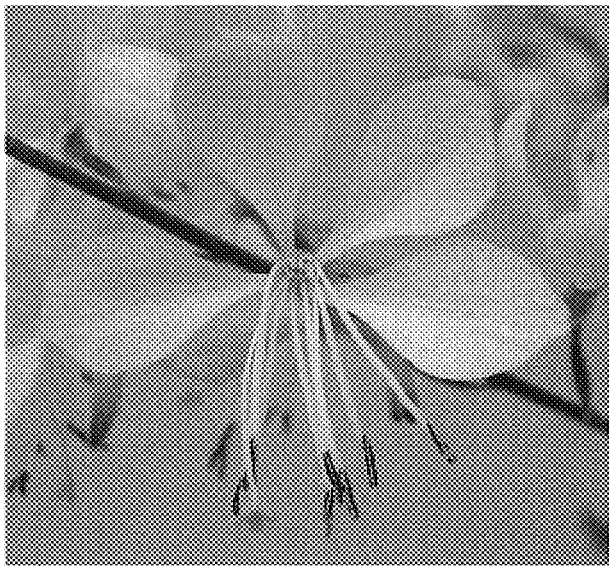
FIG. 2 illustrates a close-up view of an individual flower of 'Baltincite'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Apr. 29, 2008 between 9:00 a.m. and 11:00 a.m. under natural light conditions in West Chicago, Ill.

The following descriptions and measurements describe plants produced from cuttings from stock plants and grown in a glass-covered greenhouse under conditions comparable to those used in commercial practice. The plants were grown at West Chicago, Ill. in 4.5 inch pots for 6 weeks utilizing a soilless growth medium. Plants were given one pinch at transplant. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Gaura lindheimeri* cultivar Baltincite.

Parentage:

*Female parent.*—Proprietary *Gaura lindheimeri* breeding selection designated 0044-A2, not patented.

*Male parent.*—Proprietary *Gaura lindheimeri* breeding selection designated 0017-A1-B2-A2-2, not patented.

Propagation:

*Type cutting.*—Terminal stem.

*Time to initiate roots.*—Approximately 10 to 14 days.

*Time to produce rooted cutting.*—Approximately 24 to 28 days.

*Root description.*—Fibrous.

*Rooting habit.*—Fibrous.

Plant description:

*Commercial crop time.*—Approximately 7 to 10 weeks from a rooted cutting to finish in an 11 cm pot.

*Growth habit and general appearance.*—Moderately vigorous, upright growth habit.

*Size.*—Height from soil level to top of plant plane: Approximately 40.1 cm. Width: Approximately 32.5 cm.

*Branching habit.*—Freely branching, pinching improves habit. Quantity of main branches per plant: Approximately 4.

*Branch.*—Strength: Strong. Length: Approximately 36.2 cm. Diameter at central internode: Approximately 2.0 mm. Length of central internode: Approximately 2.4 cm. Texture: Sparsely pubescent. Color of young and mature stems: 137A.

Foliage description:

*General description.*—Quantity of leaves per main branch: Approximately 10. Fragrance: None. Form: Simple, sessile. Arrangement: Alternate.

*Leaves.*—Aspect: Perpendicular to stem, turning downward with age. Shape: Oblanceolate. Margin: Slightly dentate. Apex: Acute. Base: Attenuate. Venation pattern: Pinnate. Length: Approximately 6.8 cm. Width: Approximately 1.5 cm. Texture of upper surface: Glabrous. Texture of lower surface: Sparsely pubescent. Color of upper surface of young foliage: 137A with indistinguishable venation. Color of lower surface of young foliage: 137B with indistinguishable venation. Color of upper surface of mature foliage: Darker than 137A with venation of 146B. Color of lower surface of mature foliage: Closest to 137A with venation of 146B.

Inflorescence description:

*General description.*—Type: Spicate raceme. Quantity per plant: Approximately 4. Fragrance: Slight. Length or height: Approximately 24.8 cm. Width: Approximately 5.5 cm. Quantity of fully open flowers per inflorescence: Approximately 4.

*Peduncle.*—Strength: Strong. Aspect: Erect. Length: Approximately 4.3 cm. Diameter: Approximately 1.5 mm. Texture: Sparsely pubescent. Color: 137A.

Flowering description:

*Flowering habit.*—'Baltincite' is freely flowering under outdoor growing conditions with substantially continuous blooming from spring through autumn and year-round in greenhouse environment.

*Lastingness of individual flower on the plant.*—Approximately 2 to 3 days.

Flower description:

*General description.*—Type: Single, zygomorphic, not persistent, sessile.

*Bud.*—Shape: Tubular. Length: Approximately 2.6 cm. Diameter: Approximately 2.0 mm. Texture: Sparsely pubescent. Color: Base of 143C with an overlay of 182A, transitions at sepal attachment to 145C with 143A at apex.

*Corolla.*—Length: Approximately 3.1 cm. Width: Approximately 3.8 cm. Depth: Approximately 3.2 cm.

*Petals.*—Quantity: 4, in a single whorl. Shape: Obovate. Appearance: Satiny. Margin: Entire. Apex: Broadly acute. Base: Attenuate. Length Approximately 1.8 cm. Width: Approximately 9.0 mm. Texture of upper and lower surfaces: Glabrous. Color of upper and lower surfaces when fully open: Purer white than 155D; during senescence develops an overlay of 62C.

*Calyx.*—Shape: Frequently fused at the apex when the flower is opening. Sometimes they remain fused and fail to separate after flower opens. Diameter: Approximately 4.0 mm.

*Sepals.*—Quantity per flower: 4. Shape: Linear, reflexed. Apex: Fused or acute. Length: Approximately 1.6 cm. Width: Approximately 2.0 mm. Texture of upper surface: Glabrous. Texture of lower surface: Sparsely pubescent. Color of upper surface: 145D with 143B at apex; during senescence develops a strong overlay of 62C with 184B at apex. Color of lower surface: 145C with 143A at apex; during senescence develops a strong overlay of 62C with 184B at apex.

*Reproductive organs.*—Androecium: Stamen quantity: 8. Stamen length: Approximately 1.8 cm. Filament color: Pure white. Anther shape: Linear. Anther length: Approximately 4.0 mm. Anther color: 187A. Pollen amount: Abundant. Pollen color: 10D. Gynoecium: Pistil quantity: 1 per flower. Pistil length: Approximately 3.2 cm. Stigma shape: 4 lobed. Stigma color: 144C. Style color: 145C. Ovary position: Inferior. Ovary length: Approximately 8.0 mm. Ovary color: 143C with an overlay of 182A.

Seed and fruit production: Neither seed nor fruit production has been observed.

Disease and pest resistance: Resistance to pathogens and pests common to *Gaura* has not been observed.

What is claimed is:

1. A new and distinct cultivar of *Gaura* plant named 'Baltincite', substantially as herein shown and described.

* * * * *